(12) United States Patent
Lee et al.

(10) Patent No.: US 11,697,637 B2
(45) Date of Patent: Jul. 11, 2023

(54) ANTI-FREEZING COMPOSITION

(71) Applicant: GWANGJU INSTITUTE OF SCIENCE AND TECHNOLOGY, Gwangju (KR)

(72) Inventors: Eunji Lee, Gwangju (KR); Nayeong Jeon, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 17/856,425

(22) Filed: Jul. 1, 2022

(65) Prior Publication Data
US 2023/0023403 A1 Jan. 26, 2023

(30) Foreign Application Priority Data
Jul. 2, 2021 (KR) .......... 10-2021-0086937

(51) Int. Cl.
| C07D 209/04 | (2006.01) |
| A01N 1/02 | (2006.01) |
| C09K 5/20 | (2006.01) |

(52) U.S. Cl.
CPC ............ C07D 209/04 (2013.01); A01N 1/02 (2013.01); C09K 5/20 (2013.01)

(58) Field of Classification Search
CPC .......... C07D 209/04; A01N 1/02; C09K 5/20
See application file for complete search history.

(56) References Cited

U.S. PATENT DOCUMENTS

2015/0153194 A1* 6/2015 Udeshi ............... G01C 21/3691
701/117

FOREIGN PATENT DOCUMENTS

KR 10-1396925 B1 5/2014

* cited by examiner

*Primary Examiner* — Kamal A Saeed
(74) *Attorney, Agent, or Firm* — The PL Law Group, PLLC (57) ABSTRACT

An anti-freezing composition according to an embodiment of the present disclosure includes at least one of a compound represented by Formula 1 and a compound represented by Formula 2. An anti-freezing composition according to another embodiment of the present disclosure includes a peptide consisting of amino acids having different chirality, thereby having an excellent effect of inhibiting ice formation or ice recrystallization.

8 Claims, 9 Drawing Sheets

ANTI-FREEZING COMPOSITION

CROSS-REFERENCE TO RELATED APPLICATION AND CLAIM OF PRIORITY

This application claims the benefit under 35 USC § 119 of Korean Patent Application No. 10-2021-0086937, filed on Jul. 2, 2021, in the Korean Intellectual Property Office, the entire disclosure of which is incorporated herein by reference for all purposes.

BACKGROUND

1. Field of the Invention

The present invention relates to an anti-freezing composition.

2. Description of the Related Art

A cryoprotective agent (CPA) is a compound capable of reducing ice crystal formation or inhibiting ice crystal growth in a solution exposed to a temperature below zero (0) ° C. when present in the solution. As the CPA, small molecules, synthetic polymers, and cryoprotective proteins are mainly used in the art.

Organ transplantation is the best treatment for end-stage organ failure in terms of a survival rate, quality of life, and cost effectiveness. Unfortunately, there is a long time gap between supply and demand of organ implants, which is one of important medical barriers that make patients who need organ transplantation live a hard life for a long period of waiting time. One of the reasons for low supply of organs is caused by the absence of a reliable preservation method.

In order to properly preserve the organ, it is necessary to wash the organ with a preservation solution to remove blood, and stabilize the organ. Even after stabilizing the organ in the preservation solution, an available time for assignment, transport, and transplantation of the organ after removal from the donor is commonly limited to 6 to 12 hours. Due to such a short time, there is a limitation that most of the organs will be transplanted to a patient within a short distance, which results in a significant reduction in the opportunity of organ transplantation for a patient in a remote place due to travel-time constraints. Such a shortage of clinically available organs has led to an increase in illegal organ transactions and human trafficking, despite laws for prohibiting the sale of human organs in almost every country.

Current CPAs used in organ preservation generally include, in particular, ethylene glycol, 1,2-propanediol, dimethyl sulfoxide, formamide, glycerol, sucrose, lactose or D-mannitol. In order to reduce or inhibit ice crystal growth at a temperature required for organ preservation, an effective concentration of the CPAs should be very high, usually 60% or more. It is known that at such a high concentration, these compounds may be toxic to tissues that are trying to be preserved by the same, and when removing large amounts of CPAs along with increasing the temperature prior to the transplantation may result in irreversible cell death.

Other CPAs used to reduce or inhibit ice crystal formation include synthetic polymers and cryoprotective proteins. Similar to the CPAs described above, each of them has their own drawbacks. For example, antifreeze proteins (AFPs) existing in nature, such as proteins isolated from fishes, plants, or insects, are highly effective in preventing ice formation, but currently available cryoprotective proteins are expensive in terms of production costs as well as have a low purity. Thereby, it is considered to be inefficient to use them in the industry.

Meanwhile, it is known that chemical cryoprotectants, for example, dimethyl sulfoxide (DMSO) cause side effects such as fever, or itchiness, etc., and exhibit biotoxicity such as degeneration of the brain or acting as a neurotoxin. Therefore, the chemical cryoprotectants described above have a disadvantage in that it is difficult to use when freezing cells, tissues, organs or food, etc.

SUMMARY

It is an object of the present invention to provide an anti-freezing composition.

Another object of the present invention is to provide a composition for cell or tissue cryopreservation.

In addition, another object of the present invention is to provide a composition for food cryopreservation.

Further, another object of the present invention is to provide a composition for drug cryopreservation.

Furthermore, another object of the present invention is to provide an anti-freezing method.

To achieve the above objects, the following technical solutions are adopted in the present invention.

1. An anti-freezing composition comprising at least one of compounds represented by Formula 1 or 2 below:

[Formula 1]

(In Formula 1 above, $R_1$ is —OH or —$NH_2$),

[Formula 2]

(In Formula 2 above, $R_2$ is —OH or —$NH_2$).

2. The anti-freezing composition according to the above 1, wherein the anti-freezing composition comprises the compound represented by Formula 1 and the compound represented by Formula 2 in a molar ratio of 1:1.

3. A composition for cell or tissue cryopreservation comprising the composition of the above 1 or 2.

4. A composition for food cryopreservation comprising the composition of the above 1 or 2.

5. A composition for drug cryopreservation comprising the composition of the above 1 or 2.

6. An anti-freezing method comprising adding the composition of the above 1 or 2 to a sample subject to cryopreservation.

7. The anti-freezing method according to the above 6, wherein the sample is at least one selected from the group consisting of cells, tissues, foods and drugs.

The anti-freezing composition of the present invention may have an excellent effect of inhibiting ice formation or ice recrystallization, thus to help cryopreservation of cells, tissues, foods or drugs.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Hereinafter, the present invention will be described.

The present invention provides an anti-freezing composition.

The anti-freezing composition may include a peptide (Fmoc-WWT) in which a fluorenyl methoxycarbonyl (Fmoc) group is bound to N terminal of a sequence consisting of tryptophan (W)-tryptophan (W)-threonine (T). The peptide may have an amidated C terminal.

Chirality of the amino acid of the peptide may be $^L$W$^L$W$^D$T or $^D$W$^D$W$^L$T. The left superscript L or D of the amino acid indicates that the corresponding amino acid is a laevorotatory (L) form amino acid or dextrorotatory (D) form amino acid, respectively.

The anti-freezing composition may include at least one of compounds represented by Formula 1 or 2 below.

[Formula 1]

(In Formula 1 above, R$_1$ is —OH or —NH$_2$),

[Formula 2]

(In Formula 2 above, R$_2$ is —OH or —NH$_2$).

The anti-freezing composition may include the compound represented by Formula 1 and the compound represented by Formula 2 in a molar ratio of 1:1.

The fluorenyl methoxycarbonyl (Fmoc) group is a group represented by Formula 3 below.

[Formula 3]

The Fmoc group induces intermolecular π-π stacking, and the tryptophan (W)-tryptophan (W) bound to the Fmoc group is also self-assembled by intermolecular π-π stacking to form a β-sheet structure similar to the secondary structure of the protein. Through this arrangement, residues bound to the C terminal of tryptophan, which can interact with water, are arranged outward of the self-assembly to perform hydrophilic interactions or hydrophobic interactions with an ice interface, or form hydrogen bonds with an ice interface. For example, when the residue bound to the C terminal of tryptophan is threonine (T) (i.e., Fmoc-WWT), a hydroxyl group (—OH), which is a hydrophilic functional group of threonine, is bound to the crystal surface of ice, and a methyl group (—CH$_3$), which is a hydrophobic functional group, serves to inhibit access of other water molecules, such that it may exhibit excellent ice recrystallization inhibition activity.

As used herein, the term "chirality" refers to hand symmetry, and a chiral structure or molecule means a structure or molecule whose image is not superimposed with its mirror-reflected shape. Most amino acids in nature have chirality in the laevorotatory (L) form. Further, in the case of antifreeze proteins/peptides (AFPs) existing in nature, all amino acids constituting the same have chirality in the L form.

The present inventors have paid attention to the fact that a direction in which AFPs consisting only of D-form amino acids are bound to the ice crystal plane is opposite to that of AFPs consisting only of L-form amino acids, thus to prepare a peptide including both L-form amino acids and D-form amino acids, and had confirmed excellent antifreezing effect thereof.

Chiralities of the second amino acid and the third amino acid of the peptide included in the anti-freezing composition of the present invention are opposite to each other. Therefore, the peptide effectively targets a pyramidal plane exposed during ice growth, thereby exhibiting an excellent effect of inhibiting ice recrystallization.

In one embodiment, when the chiralities of tryptophan (W), which is the second amino acid of the peptide, and threonine (T), which is the third amino acid, are opposite to each other (e.g., in the case of Fmoc-$^L$W$^L$W$^D$T or Fmoc-$^D$W$^D$W$^L$T), the direction of an indole group, which is a hydrophobic functional group of the second tryptophan and the direction of a methyl group of threonine are the same as each other, thereby further strongly inhibiting access of water molecules. Therefore, it is possible to exhibit superior ice recrystallization inhibition activity than the case where the peptide is Fmoc-$^L$W$^L$W$^L$T or Fmoc-$^D$W$^D$W$^D$T.

In one embodiment, a mixture in which Fmoc-$^L$W$^L$W$^D$T and Fmoc-$^D$W$^D$W$^L$T peptides are mixed in a molar ratio of 1:1 may exhibit superior ice recrystallization inhibition activity than the mixture in which Fmoc-$^L$W$^L$W$^L$T and Fmoc-$^D$W$^D$W$^D$T peptides are mixed in a molar ratio of 1:1.

Ice crystals can grow through ice recrystallization, which refers to a process of growing from small ice crystals to larger ice crystals, and the growth thereof occurs according to an Ostwald ripening mechanism. Ostwald ripening may be performed in a dissolution-diffusion-refreezing or a sublimation-diffusion-condensation mechanism. In other words, the growth of ice crystals does not occur as the ice crystals are adhered to each other, but rather as small ice crystals are melted between the crystals, and spread toward large ice crystals, then to be a part of large ice crystals while refreezing.

Anti-freezing refers to actions of lowering a freezing point, preventing ice formation or lowering a speed of ice formation, preventing ice recrystallization, lowering a speed of ice recrystallization, or maintaining a size of ice crystals to be small. As used herein, the term "anti-freezing" may be used interchangeably with "antifreezing," "freezing control," "freeze control," "freezing suppression" and "freeze inhibition."

The anti-freezing composition of the present invention has excellent anti-freezing effect as well as includes amino acids to exhibit biocompatibility, such that it may be used for cryopreservation of cells/tissues, foods or drugs. In addition, the compounds included in the anti-freezing composition of the present invention have an advantage of being easy to mass-produce as they are peptides consisting of a relatively short sequence.

The anti-freezing composition of the present invention may further include a material having an anti-freezing ability known in the prior art. The anti-freezing composition may further include, for example, dimethyl sulfoxide (DMSO), glycerol, 1,2-propanediol, sucrose, glucose, proline, galactose, lactose, glycine betaine, or fructose. In addition, when using the anti-freezing composition for cell cryopreservation or food cryopreservation, it may further include sucrose, glucose, lactose, glycine betaine, or fructose, which has low cytotoxicity.

The present invention provides a composition for cell or tissue cryopreservation.

The composition for cell or tissue cryopreservation includes the above-described anti-freezing composition.

Cryopreservation is a method of storing an object to be preserved in a cryogenic (ultra-low temperature) state through a process of freezing the same, and then thawing it when necessary. Upon cryopreservation, all biological activities including biochemical reactions that lead to cell death are effectively halted.

When cryopreserving cells or tissues, ice recrystallization may occur in the process of thawing the frozen cells or tissues at the time of trying to use them later. When ice recrystallization occurs, as the ice crystals grow, the cell membrane is damaged and cell dehydration occurs, thereby resulting in damaging the cells and tissues. Organisms living in a lower-temperature environment may be more easily damaged by the ice recrystallization.

The composition for cell or tissue cryopreservation of the present invention may inhibit ice growth or recrystallization, thereby preventing cells or tissues from dying due to ice crystal growth.

The composition for cell or tissue cryopreservation of the present invention may be applicable to all cells or tissues that are commonly used by freezing for preservation.

Cells to be applied may include, for example, prokaryotic cells; eukaryotic cells; microorganisms; animal cells; cancer cells, sperms; eggs; stem cells including adult stem cells, embryonic stem cells, and dedifferentiated stem cells; blood cells including cord blood, white blood cells, red blood cells, and platelets; and tissue cells including kidney cells, liver cells, and muscle cells, but they are not limited thereto. The cells to be applied may include, for example, human embryonic kidney (293T) cells, non-tumorigenic lung bronchial epithelial (BEAS-2B) cells, or lung carcinoma epithelial (A549) cells, but they are not limited thereto.

Tissues to be applied may include, for example all tissues such as cornea, kidney, heart, small intestine, pancreas, lung, liver, and the like, but they are not limited thereto.

The composition for cell or tissue cryopreservation of the present invention may include a cryopreservation liquid for cryopreservation of cells and tissues in addition to the above-described anti-freezing composition. The cryopreservation liquid may include water, saline, phosphate buffered saline (PBS), various cell culture liquids, and the like, but it is not limited thereto.

The present invention provides a composition for food cryopreservation.

The composition for food cryopreservation includes the above-described anti-freezing composition.

Cryopreservation may be defined within the above-described range, but it is not limited thereto.

When cryopreserving food, ice recrystallization may occur in the process of thawing the frozen food at the time of trying to use it later. When ice recrystallization occurs, ice crystals generated from moisture grow, which destroys cells or tissues present in food, thereby resulting in degradation of taste.

The composition for food cryopreservation of the present invention may inhibit ice growth or recrystallization, thereby preventing a change in the osmotic pressure due to ice crystal growth or death of cells or tissues in food, and thereby minimizing quality degradation of food.

The composition for food preservation of the present invention may be applicable to all foods that are commonly used by freezing for preservation. Food to be applied may include meats, fishes and shellfishes, fruits and vegetables, but it is not limited thereto.

The present invention provides a composition for drug cryopreservation.

The composition for drug cryopreservation includes the above-described anti-freezing composition.

Cryopreservation may be defined within the above-described range, but it is not limited thereto.

When cryopreserving drugs, ice recrystallization may occur in the process of thawing the frozen drugs at the time of trying to use them later. When ice recrystallization occurs, ice crystals generated from moisture grow, and as the ice crystals grow, cell membranes are damaged and cell dehydration occurs, thereby causing damage to the cells and tissues present in the drugs.

The composition for drug cryopreservation of the present invention may inhibit ice growth or recrystallization, thereby preventing the death of cells or tissues in the drugs due to ice crystal growth, and thereby minimizing quality degradation of the drugs.

The composition for drug cryopreservation of the present invention may be applicable to all drugs used by freezing for normal preservation. The drugs to be applied may be prepared using, for example, cells or tissues.

The present invention provides an anti-freezing method.

The anti-freezing method includes adding the above-described anti-freezing composition to a sample subject to cryopreservation.

Anti-freezing may be defined within the above-described range, but it is not limited thereto.

The anti-freezing method may be a method of suppressing the freezing of the sample by adding the above-described anti-freezing composition to the sample to inhibit ice growth or recrystallization.

The sample to be subjected to antifreeze may include at least one selected from the group consisting of cells, tissues, foods, and drugs.

The cells, tissues, foods and drugs may be defined within the above-described range, but it is not limited thereto.

Hereinafter, the present invention will be described in detail with reference to examples.

EXAMPLE

In order to suppress the ice recrystallization phenomenon which affects cell damage, the present inventors have developed a biocompatible/biodegradable peptide-based cryoprotectant, of which chiralities of amino acids are adjusted, in consideration of an interaction between the crystal plane of ice and functional groups.

Self-assembly technique was applied to the peptide consisting of less than 10 amino acids, and the interaction thereof with a specific crystal plane of ice according to the chirality of the peptide was investigated. By using a heterochiral peptide which is not present in nature, a difference in the degree of anti-freezing effect according to the chirality of amino acids was confirmed. Based on the freezing control technique derived from the present example, it is believed that the peptide may be applied to food and drug freeze/thaw preservatives having guaranteed biocompatibility and sample stability, which will be described in detail below.

1. Design and Preparation of Peptide (Fmoc-WWT-NH$_2$)

Figure 1:
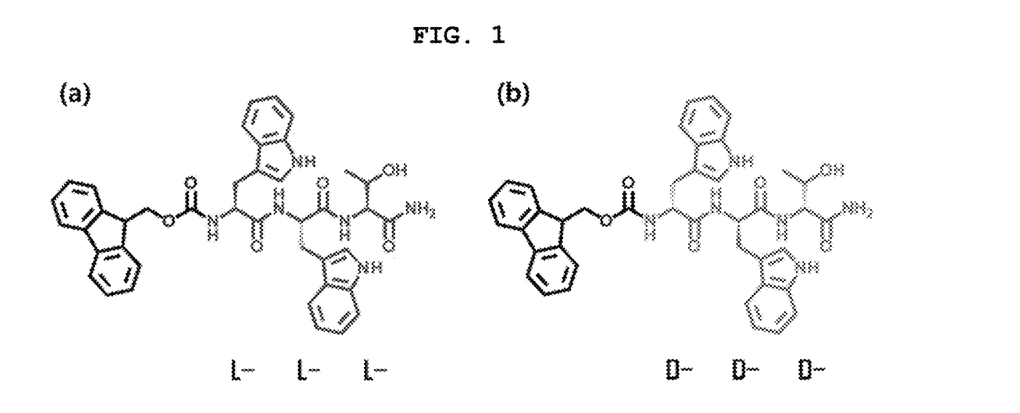
FIG. 1 illustrates structures of fluorenyl methoxycarbonyl (Fmoc)-$^L$W$^L$W$^L$T and Fmoc-$^D$W$^D$W$^D$T peptides.
Figure 2:
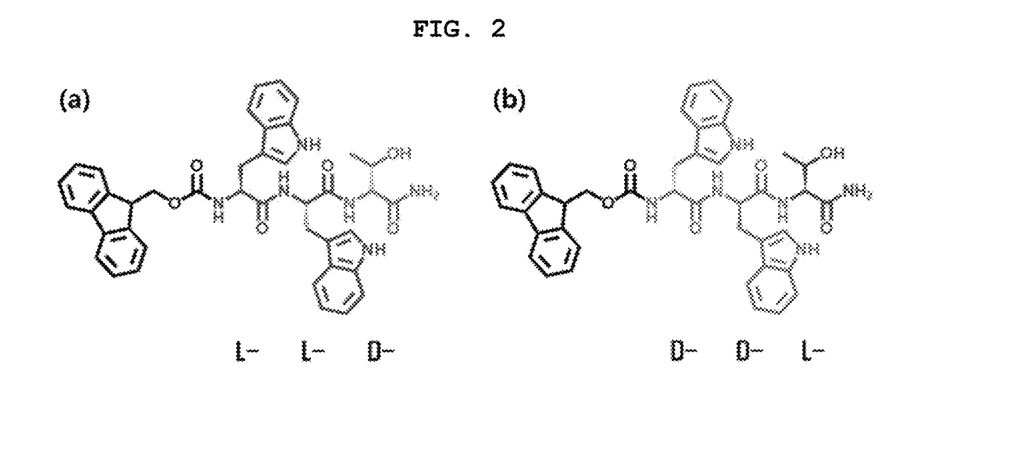
FIG. 2 illustrates structures of Fmoc-$^L$W$^L$W$^D$T and Fmoc-$^D$W$^D$W$^L$T peptides.

The present inventors have designed an anti-freezing peptide (Fmoc-WWT) using Fmoc-WW scaffolds. The Fmoc-WW scaffold grows in a fibril structure, and is capable of label-free optical sensing due to light-emitting properties of the WW dipeptide. In addition, the present inventors have predicted that a direction in which the Fmoc-WWT-NH$_2$ peptide ((b) of FIG. 1) having chirality of amino acid, $^DW^DW^DT$, is bound to ice opposite appears to the direction in which the $^LW^LW^LT$ peptide ((a) of FIG. 1) is bound to ice, and prepared $^LW^LW^DT$ ((a) of FIG. 2) and $^DW^DW^DT$ ((b) of FIG. 2) peptides having different chiralities of amino acids in the peptide based on the prediction.

Each amino acid Fmoc-Trp-OH, Fmoc-Thr(tert-butyl, (tBu))-OH and Rink Amide MBHA resin for preparation of peptides were purchased from Merck, solvents were purchased from Daejung Chemical for HPLC, and other reagents were purchased from Merck.

Fmoc-WWT was synthesized on Rink Amide MBHA resin (100-200 mesh) using a standard method of solid-phase peptide synthesis in a CEM Focused Microwave™ Synthesis System, Discover (CEM corporation, Mathews, USA). The resin was washed with dichloromethane (DCM, 99.5%), then the resin was expanded in a mixture in which N,N-dimethylformamide (DMF, 99.5%) and DCM were mixed in a ratio of 1:1 in a stirring culture apparatus for 30 minutes. The Fmoc portion of the resin was removed in the microwave for 3 minutes using 20% piperidine within DMF, and thoroughly washed with DMF, DCM and N-methylpyrrolidone (NMP, 99.7%). Thereafter, in order to prepare Fmoc-$^LW^LW^LT$-NH$_2$ and Fmoc-$^DW^DW^LT$-NH$_2$, an NMP solution, in which Fmoc-L-Thr(tBu)-OH (5.0 equiv.); 2-(1H-benzotriazol-1-yl)-1,1,3,3-tetra-methyluronium hexafluoro phosphate (HBTU) (4.9 equiv.); and N-ethyldiisopropylamine (DIPEA, 99%) (5.0 equiv.) were mixed, was added to the resin, and treated in the microwave for 10 minutes. Then, in order to prepare Fmoc-$^D$W$^D$W$^D$T-NH$_2$ and Fmoc-$^L$W$^L$W$^D$T-NH$_2$, an NMP solution, in which Fmoc-D-Thr(tert-butyl, (tBu))-OH (5.0 equiv.); 2-(1H-benzotriazol-1-yl)-1,1,3,3-tetra-methyluronium hexafluoro phosphate (HBTU) (4.9 equiv.); and N-ethyldiisopropylamine (DIPEA, 99%) (5.0 equiv.) were mixed, was added to the resin, and treated in the microwave for 10 minutes. Thereafter, (Fmoc)-L-Trp-OH (5.0 equiv.) was used to prepare Fmoc-$^L$W$^L$T-NH$_2$ and Fmoc-$^L$W$^L$W$^D$T-NH$_2$, followed by coupling with the N terminal of the peptide on the resin in a sequence from Fmoc-WW-resin. Then, Fmoc-D-Trp-OH (5.0 equiv.) was used to prepare Fmoc-$^D$W$^D$W$^D$T-NH$_2$ and Fmoc-$^D$W$^D$W$^L$T-NH$_2$, followed by coupling with the N terminal of the peptide on the resin in a sequence from Fmoc-WW-resin. For each of coupling and protective group removing processes, the presence of a free amino group was confirmed through the Kaiser test.

The resin was treated with a cleavage solution (trifluoroacetic acid (TFA):Triisopropylsilane (TIS):H$_2$O=95:2.5:2.5) in a stirring culture apparatus for 2 hours. Excessive TFA was removed with nitrogen gas, and the product was precipitated in cold diethyl ether (Et$_2$O, 99%), then centrifuged at 4000 rpm for 5 minutes. Peptides were purified by YL9100 high performance liquid chromatography (HPLC, Young Lin Instrument Co., Ltd., Anyang, Republic of Korea) on a C18 column (SUPELCO, Discovery, Young Lin Instrument Co., Ltd., 5 µL, 10×250 mm) at a flow rate of 2 mL min$^{-1}$. The peptide using a linear gradient of water (0.1% TFA) and acetonitrile (0.1% TFA), and confirmed by UV absorption spectra at 230 nm and 254 nm, respectively. A molecular weight of Fmoc-WWT-NH$_2$ (735 [M+Na]$^+$) was conformed with Bruker Ultraflextreme matrix-assisted laser desorption/ionization time-of-flight/time-of-flight (MALDI-TOF/TOF) mass spectrometer (Bruker Daltonik GmbH, Bremen, Germany) using α-cyano-4-hydroxycinnamic acid dissolved in a solution (0.1% TFA) in which acetonitrile and water were mixed in a ratio of 1:1 as a matrix.

Figure 3:
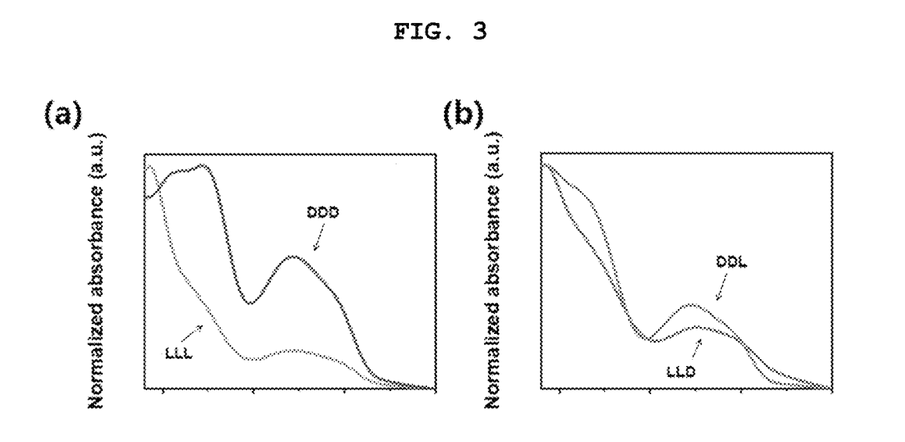
FIG. 3 illustrates ultraviolet-visible (UV-vis) absorption spectra of Fmoc-$^L$W$^L$W$^L$T, Fmoc-$^D$W$^D$W$^D$T, Fmoc-$^L$W$^L$W$^D$T and Fmoc-$^D$W$^D$W$^L$T peptides.

2. Confirmation of Characteristics of the Prepared Peptide 2-1. UV-Vis Absorption Spectrum and CD Spectrum Ultraviolet-visible (UV-vis) absorption spectra (FIG. 3) and circular dichroism (CD) spectra (FIG. 4) of the peptides prepared in the above 1 were confirmed.

The absorption spectrum was confirmed using a UH5300 UV/Vis spectrophotometer (Hitachi High-Tech Science Co., Tokyo, Japan). The absorbance of the material according to the wavelength was measured using a 4 mL quartz cell, and a baseline was set using distilled (DI) water. Then, each absorbance data of 0.1 mM AFP was measured in the DI water.

The CD spectrum of each peptide solution was measured using a Jasco J-810 circular dichroism spectrometer (Jasco Inc., Tokyo, Japan). Each 0.1 mM peptide solution was scanned at a wavelength of 190-350 nm at a rate of 500 nm/min using the 4 mL quartz cell at room temperature. The scanned data were accumulated five times and were measured at HT of 700 V or less for securing reliability of data.

Figure 4:
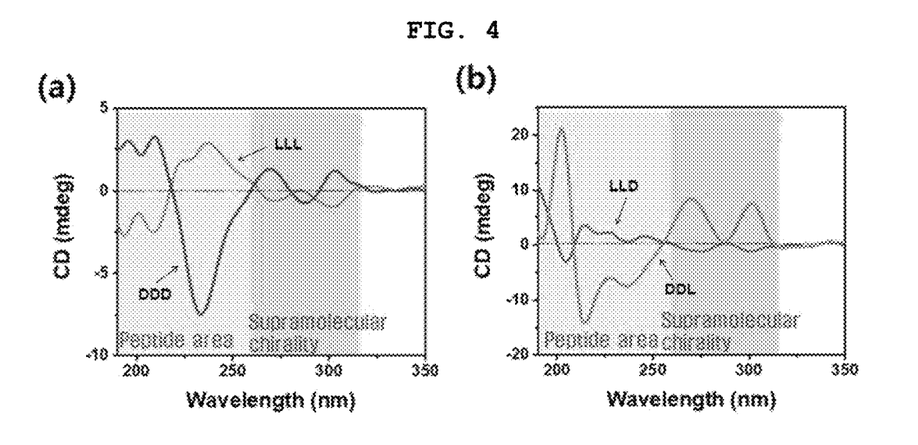
FIG. 4 illustrates circular dichroism (CD) spectra of Fmoc-$^L$W$^L$W$^L$T, Fmoc-$^D$W$^S$W$^D$T, Fmoc-$^L$W$^L$W$^D$T and Fmoc-$^D$W$^D$W$^L$T peptides.
Figure 5:
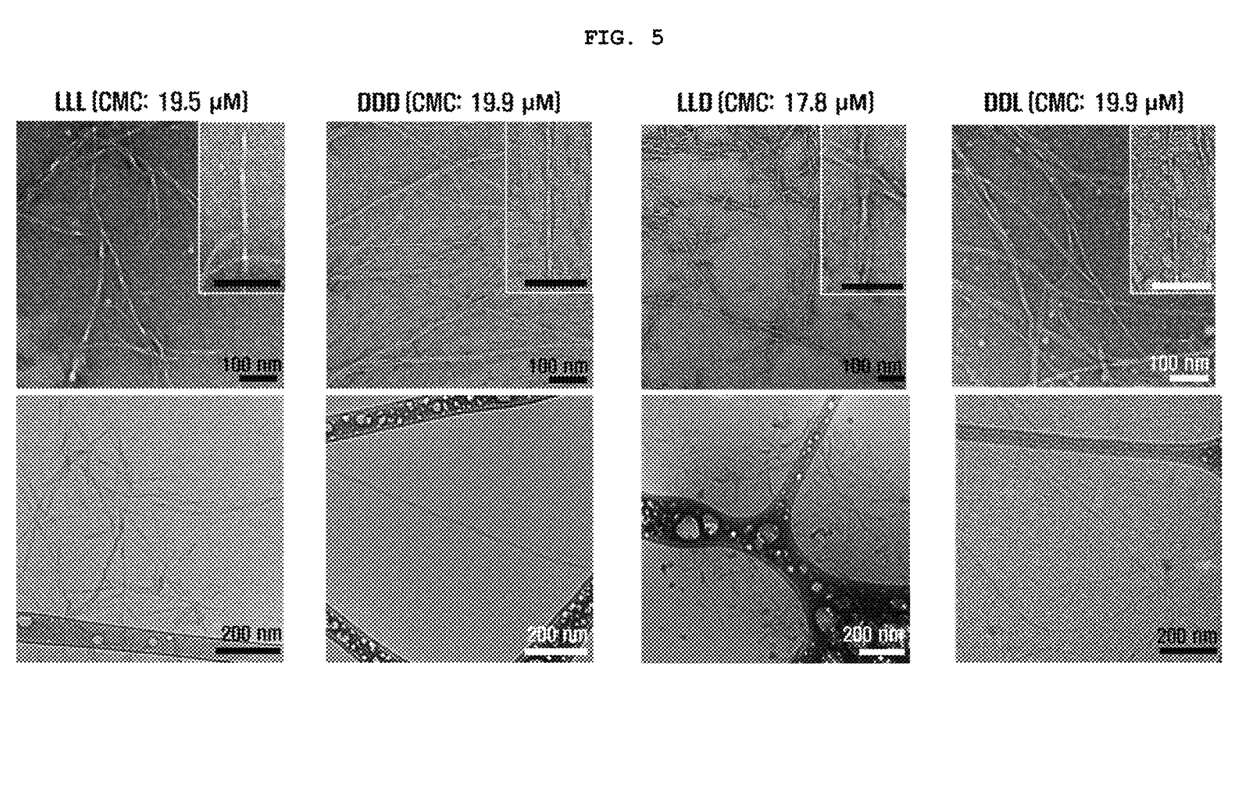
FIG. 5 illustrates transmission electron microscope (TEM) images (first line) and Cryo-TEM images (second line) of Fmoc-$^L$W$^L$W$^L$T, Fmoc-$^D$W$^D$W$^D$Y, Fmoc-$^L$W$^L$W$^D$T and Fmoc-$^D$W$^D$W$^L$T peptides.

As shown in (a) of FIG. 4, as a result of identifying the CD spectra of Fmoc-$^L$W$^L$W$^L$T-NH$_2$ and Fmoc-$^D$W$^D$W$^D$T-NH$_2$, it was confirmed that two mirror image molecules had CD values opposite to each other. In addition, it was confirmed that an antiparallel β-sheet secondary structure was formed in a peptide monomolecular region. Further, it was confirmed that a helical arrangement was formed through the π-π interaction between fluorene of Fmoc and tryptophan in the absorption region exhibiting supramolecular chirality.

As shown in (b) of FIG. 4, as a result of identifying the CD spectra of Fmoc-$^L$W$^L$W$^D$T-NH$_2$ and Fmoc-$^D$W$^D$W$^L$T-NH$_2$, it was confirmed that the two mirror image molecules had CD values opposite to each other. In addition, it was confirmed that an antiparallel β-sheet secondary structure was formed in the peptide monomolecular region. Further, it was confirmed that a helical arrangement was formed through the π-π interaction between fluorene of Fmoc and tryptophan in the absorption region exhibiting supramolecular chirality.

2-2. TEM and Cryo-TEM

Additionally, self-assembled nanostructures of the prepared peptides were confirmed through TEM and cryo-TEM.

Each peptide solution in aqueous solution was sampled on a Formvar carbon coated grid and dried at room temperature and atmospheric pressure. Uranyl acetate solution (2% by weight "wt. %") was dropped on the grid on which the samples were placed to perform dyeing for 3 minutes, and then the samples were absorbed by a filter paper. The samples were observed with a JEM-1400 (JEOL, Tokyo, Japan) operating at 120 kV, and images were taken with a 2k×2k Veleta CCD camera (Olympus Soft Imaging Solutions, Munster, Germany). Data were analyzed with image analysis software RADIUS (Olympus Soft Imaging Solutions, Munster, Germany).

Peptide solutions for a cryo-TEM experiment were prepared using a Vitrobot Mark IV (Thermo Fisher Scientific, USA) at 21° C. with 100% humidity. After 3.5 µL of the sample solution was applied to a Lacey carbon grid, excessive solution was removed by blotting for 1 second, and then the grid was rapidly frozen with liquid ethane. The grid was transferred to a Gatan 914 cryo holder (Gatan Inc., Pleasanton, Calif., USA), and imaged using a JEM-1400 (JEOL, Tokyo, Japan). Images were taken with a 2k×2k Veleta CCD camera (Olympus Soft Imaging Solutions, Munster, Germany). Data were analyzed with the image analysis software RADIUS (Olympus Soft Imaging Solutions, Munster, Germany).

It could be confirmed that the self-assembled nanostructures of each compound identified through TEM formed helical nanowires having a width of 3 to 5 nm, on which the chirality of single molecule were reflected in an aqueous solution, and it could be confirmed again through cryo-TEM that helical nanowires having a length of a micrometer were also formed in the actual aqueous solution. A threonine (T) group capable of interacting with ice is located on the surface of these nanostructure lines.

3. Confirmation of IRI Effect of the Prepared Peptide

Ice recrystallization inhibition (IRI) activity was analyzed to confirm an effect of inhibiting ice crystal growth of the peptide prepared in the above 1. The effect of IRI was confirmed through a commonly known splat assay.

IRI activity was determined based on "Charles A. Knight, John Hallett, A. L. DeVries (1988). Solute effects on ice recrystallization: An assessment technique. Cryobiology, 25(1)." 10 µL of sample was dropped onto a pre-chilled (−150° C.) cover slip surface from a height of 1.0 m to form a thin ice film. The glass cover slip having the thin ice film formed thereon was transferred to a nanoliter osmometer (Otago Osmometers, Dunedin, New Zealand) at −20° C. Thereafter, the temperature of the glass cover slip was gradually increased to −6° C. at a rate of 5 min$^{-1}$, and the sample was observed for 30 minutes. In order to observe the ice crystals, polarized optical microscope images were obtained with a polarization optical microscope in which a polarizing plate was mounted on the normal optical microscope. The polarized optical microscope images were taken using a Polarizing Microscope ECLIPSE LV100POL (Nikon, Tokyo, Japan). Thirty (30) largest domains in the field of view were selected and a mean value was calculated to assess the IRI activity. The values of each individual experiment were averaged by mean largest grain size (MLGS) analysis.

The IRI effect was determined by quantitatively analyzing the images obtained during ice recrystallization when thawed after freezing. Images showing ice recrystallization (FIG. 6) were taken over time, and quantified through mean largest grain size (MLGS) analysis (FIG. 7) of particles on the images.

Figure 6:
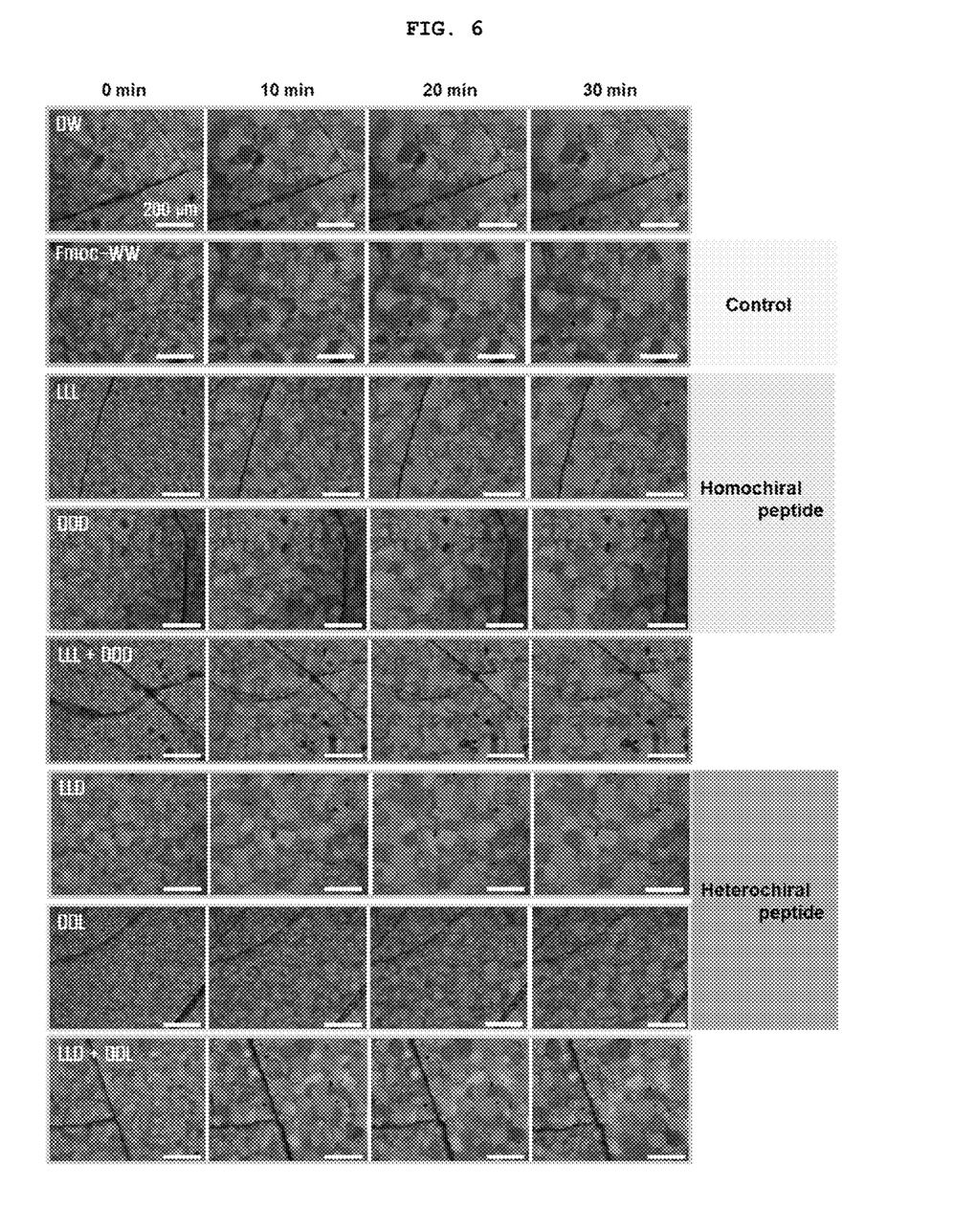
FIG. 6 illustrates results of comparing effects of inhibiting ice recrystallization in Fmoc-$^L$W$^L$W$^L$T, Fmoc-$^D$W$^D$W$^D$T, a mixture of Fmoc-$^L$W$^L$W$^L$T and Fmoc-$^D$W$^D$W$^D$T, Fmoc-$^L$W$^L$W$^D$T, Fmoc-$^D$W$^D$W$^L$T, and a mixture of Fmoc-$^L$W$^L$W$^D$T and Fmoc-$^D$W$^D$W$^L$T through a splat assay.
Figure 7:
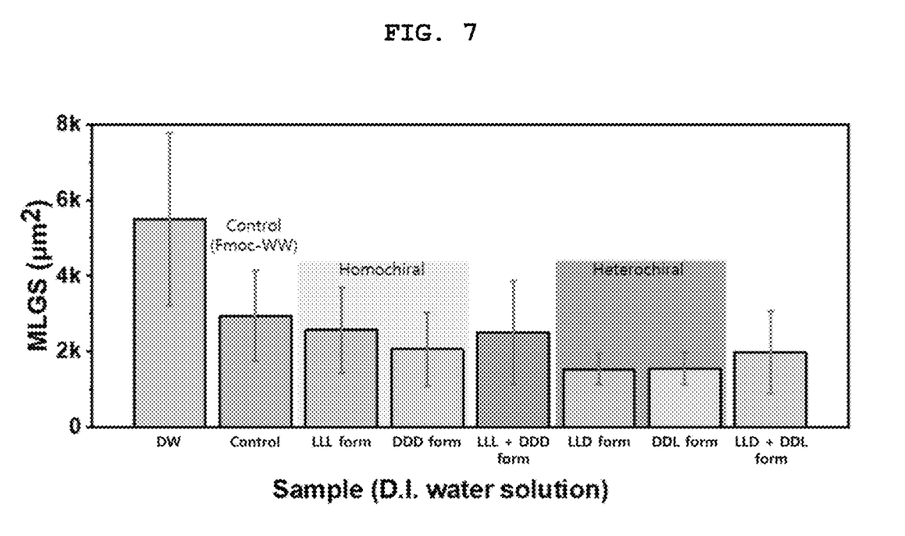
FIG. 7 illustrates the effects of inhibiting ice recrystallization in Fmoc-$^L$W$^L$W$^L$T, Fmoc-$^D$W$^D$W$^D$T, a mixture of Fmoc-$^L$W$^L$W$^L$T and Fmoc-$^D$W$^D$W$^D$T, Fmoc-$^L$W$^L$W$^D$T, Fmoc-$^D$W$^D$W$^L$T, and a mixture of Fmoc-$^L$W$^L$W$^D$T and Fmoc-$^D$W$^D$W$^L$T as a mean largest grain size (MLGS)
Figure 8:
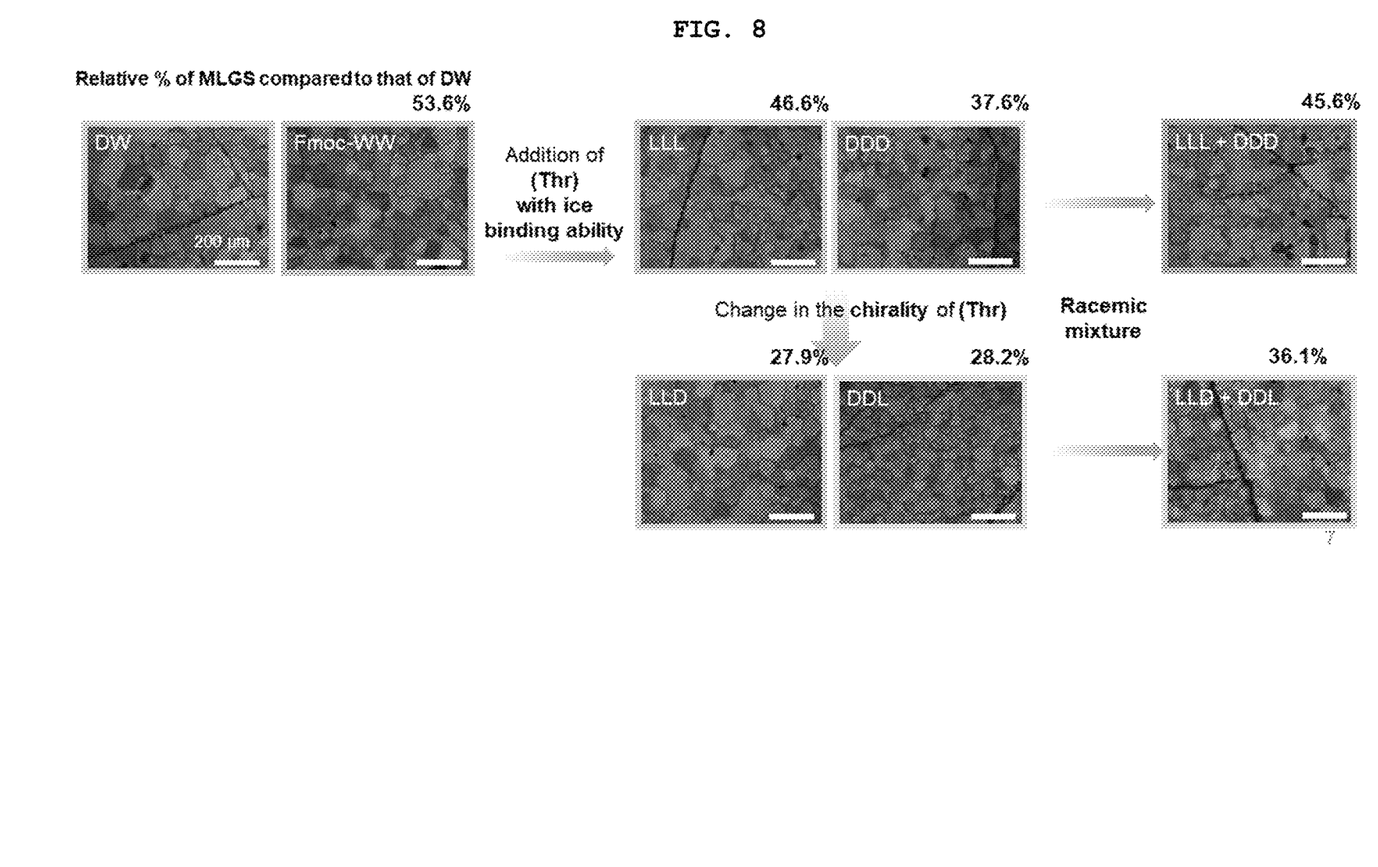
FIG. 8 illustrates relative values of the mean largest grain sizes of Fmoc-WW, Fmoc-$^L$W$^L$W$^L$T, Fmoc-$^D$W$^D$W$^D$T, a mixture of Fmoc-$^L$W$^L$W$^L$T and Fmoc-$^L$W$^L$W$^D$T, Fmoc-$^L$W$^L$W$^D$T, Fmoc-$^D$W$^D$W$^L$T, and a mixture of Fmoc-$^L$W$^L$W$^D$T and Fmoc-$^D$W$^D$W$^L$T based on the mean largest grain size when using distilled water.

When compared with a negative control, Fmoc-WW, it was confirmed that Fmoc-WWT including threonine (T) exhibited the IRI effect regardless of the chiralities of the amino acids included therein (FIGS. 6 and 7). In addition, it was observed that Fmoc-$^LW^LW^DT$-$NH_2$ (LLD form) or Fmoc-$^DW^DW^LT$-$NH_2$ (DDL form) exhibited a higher degree of IRI effect than Fmoc-$^LW^LW^LT$-$NH_2$ (LLL form) or Fmoc-$^DW^DW^DT$-$NH_2$ (DDD form) (FIGS. 6 and 7). This seems to be because in the case of Fmoc-$^LW^LW^DT$-$NH_2$ (LLD form) and Fmoc-$^DW^DW^LT$-$NH_2$ (DDL form), the direction of the indole group which is the hydrophobic functional group of the second tryptophan, and the direction of the methyl group of threonine are the same as each other, such that the effect of the hydrophobic functional groups is increased to further strongly inhibit the access of water molecules.

When compared a racemic mixture in which Fmoc-$^LW^LW^LT$-$NH_2$ (LLL form) and Fmoc-$^DW^DW^DT$-$NH_2$ (DDD form) are mixed with a racemic mixture in which Fmoc-$^LW^LW^DT$-$NH_2$ (LLD form) and Fmoc-$^DW^DW^LT$-$NH_2$ (DDL form) are mixed, it was confirmed that the case, in which Fmoc-WW and threonine (T) have different chiralities from each other, had a higher IRI effect similar to the above-described tendency.

When compared the IRI effect of a racemic mixture of "Fmoc-$^LW^LW^DT$-$NH_2$ (LLD form)" and "Fmoc-$^DW^DW^LT$-$NH_2$ (DDL form)" with the IRI effect of "a racemic mixture of Fmoc-$^LW^LW^DT$-$NH_2$ (LLD form) and Fmoc-$^DW^DW^LT$-$NH_2$ (DDL form)", the case where Fmoc-$^LW^LW^DT$-$NH_2$ (LLD form) and Fmoc-$^DW^DW^LT$-$NH_2$ (DDL form) are respectively present exhibited higher IRI effect. This seems to be because heterochiralities of the respective peptides are somewhat canceled while Fmoc-$^LW^LW^DT$-$NH_2$ (LLD form) and Fmoc-$^DW^DW^LT$-$NH_2$ (DDL form) are mixed and co-assembled.

4. Confirmation of Cryopreservation Effect of the Prepared Peptide 4-1. Cytotoxicity Test of Peptide Cytotoxicity test of the peptide prepared in the above 1 was performed by confirming cell viability using CellTiter-Glo®.

Fmoc-$^LW^LW^LT$-$NH_2$ (LLL form), Fmoc-$^DW^DW^DT$-$NH_2$ (DDD form), Fmoc-$^LW^LW^DT$-$NH_2$ (LLD form) or Fmoc-$^DW^DW^LT$-$NH_2$ (DDL form) peptide was added to human embryonic kidney (293T), non-tumorigenic lung bronchial epithelial (BEAS-2B), or lung carcinoma epithelial (A549) cell line to confirm viability of each cell.

The 293T, BEAS-2B and A549 cell lines were cultured in DMEM containing 10% FBS and 1% penicillin/streptomycin. All cell lines were cultured at 37° C. in a humid environment of 5% $CO_2$ and air. For cell viability analysis, the 293T, BEAS-2B and A549 cell lines were seeded at a density of $5 \times 10^3$ cells per 96-well culture plate with white bottom using PBS and peptide solutions at various concentrations as a control for 48 hours. Cell viability was measured with a CellTiter-Glo Luminescent Cell Viability Assay Kit according to the recommended guidelines. 100 μL of CellTiter-Glo® substrate in buffer reagent was added to each well, cultured in a shaker for 10 minutes, and incubated for 10 minutes at room temperature. Light emission signals were measured on a GloMax® Microplate Luminometer. Cytotoxicity was obtained by comparing cells treated with light emission signals to cells of the control. All experiments were independently repeated five times.

Figure 9:
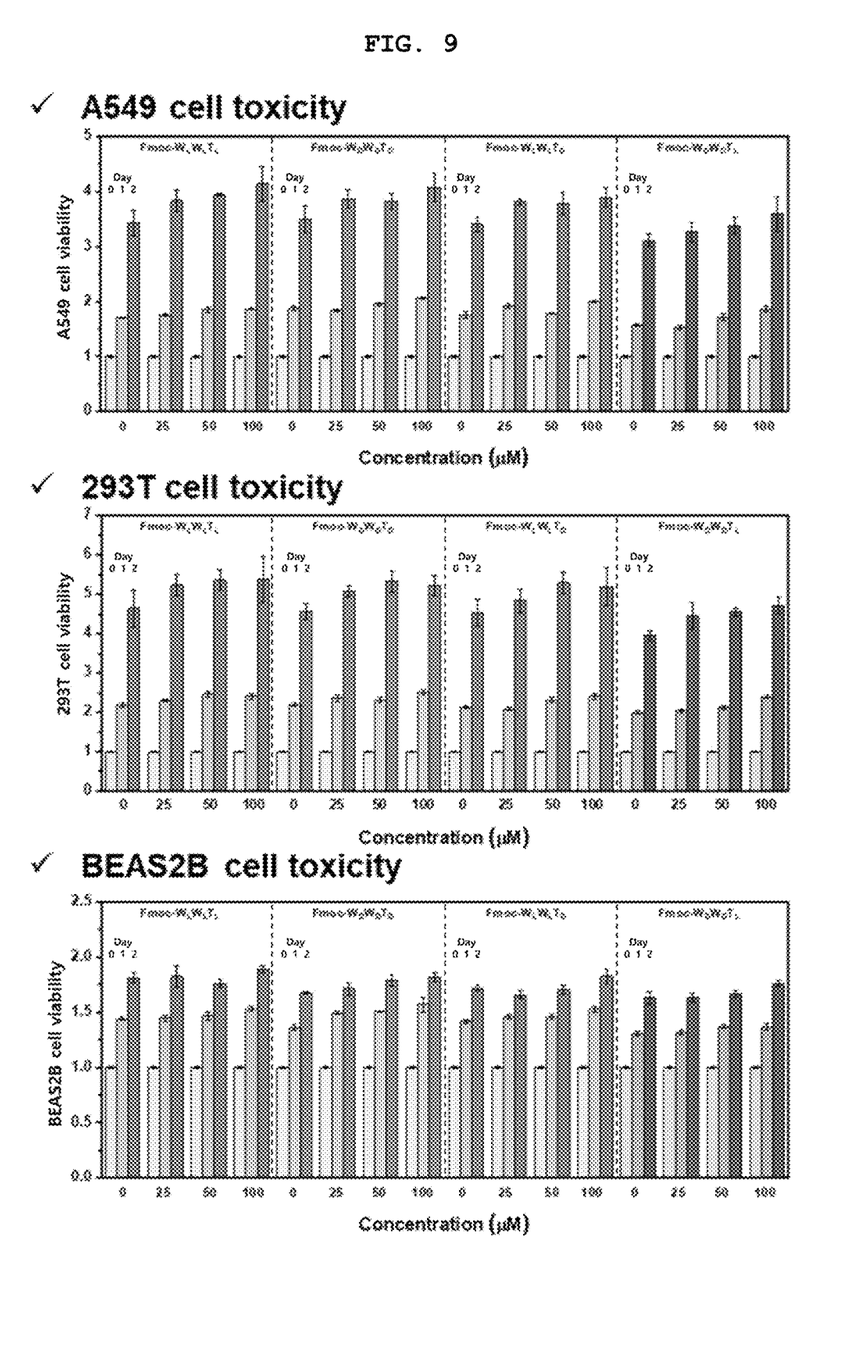
FIG. 9 illustrates results confirming that Fmoc-$^L$W$^L$W$^L$T, Fmoc-$^D$W$^D$W$^D$T, a mixture of Fmoc-$^L$W$^L$W$^L$T and Fmoc-$^D$W$^D$W$^D$T, Fmoc-$^L$W$^L$W$^D$T, Fmoc-$^D$W$^D$W$^L$T, a mixture of Fmoc-$^L$W$^L$W$^D$T and Fmoc-$^D$W$^D$W$^D$T do not exhibit toxicity on A549 cells, 293T cells and BEAS2B cells until the second day after each cell culture.

As can be seen from FIG. 9, no noticeable toxicity was observed even after cell culture for 2 days after peptide treatment, and interestingly, cell viability was further improved according to an increase in the culture time. This suggests the ability of helical peptides as cryopreservation nanoagents for both normal cells and cancer cells.

4-2. Cryopreservation Effect Test of Peptide

The cryopreservation effect test of the peptide prepared in the above 1 was performed using the human embryonic kidney (293T) cell line. Cells, which survive at 24 hours and 48 hours after 239T cells were treated with the peptide, and cryopreserved then thawed, followed by seeding, were observed to confirm recovery of the cells.

Cryopreservation effects of Fmoc-$^LW^LW^LT$-$NH_2$ (LLL form), Fmoc-$^DW^DW^DT$-$NH_2$ (DDD form), Fmoc-$^LW^LW^DT$-$NH_2$ (LLD form), Fmoc-$^DW^DW^LT$-$NH_2$ (DDL form) peptide, a racemic mixture, in which Fmoc-$^LW^LW^LT$-$NH_2$ (LLL form) and Fmoc-$^DW^DW^DT$-$NH_2$ (DDD form) were mixed in a molar ratio of 1:1, and a racemic mixture, in which Fmoc-$^LW^LW^DT$-$NH_2$ (LLD form) and Fmoc-$^DW^DW^LT$-$NH_2$ (DDL form) were mixed in a molar ratio of 1:1, were confirmed. As a negative control, Fmoc-$^LW^LW$ peptide was used.

293T cells were seeded at a density of $5 \times 10^5$ cells per vial. Cells were put in a solution consisting of 60% (v/v) medium, 40% (v/v) FBS and 25 μM of peptide in a total volume of 500 μL. Deionized water and 10% (v/v) DMSO were set as the control. The cells were frozen in a freezer to −80° C. at a rate of 1° C./min for 24 hours. Then, the frozen cell stocks were stored in a liquid nitrogen tank for 24 hours. The frozen cell stocks were rapidly thawed by incubation in a water bath at 37° C. for 2 minutes. A mixture of the frozen cell stocks was transferred to 4.5 mL medium in a 15 mL tube, and centrifuged at 1000 rpm for 3 minutes. Cell pellets were suspended in 1 mL complete medium, and seeded on a 6-well plate. The seeded cells were cultured in a humidified atmosphere for 24 hours to analyze cryopreservation efficacy of the peptides.

Figure 10A:
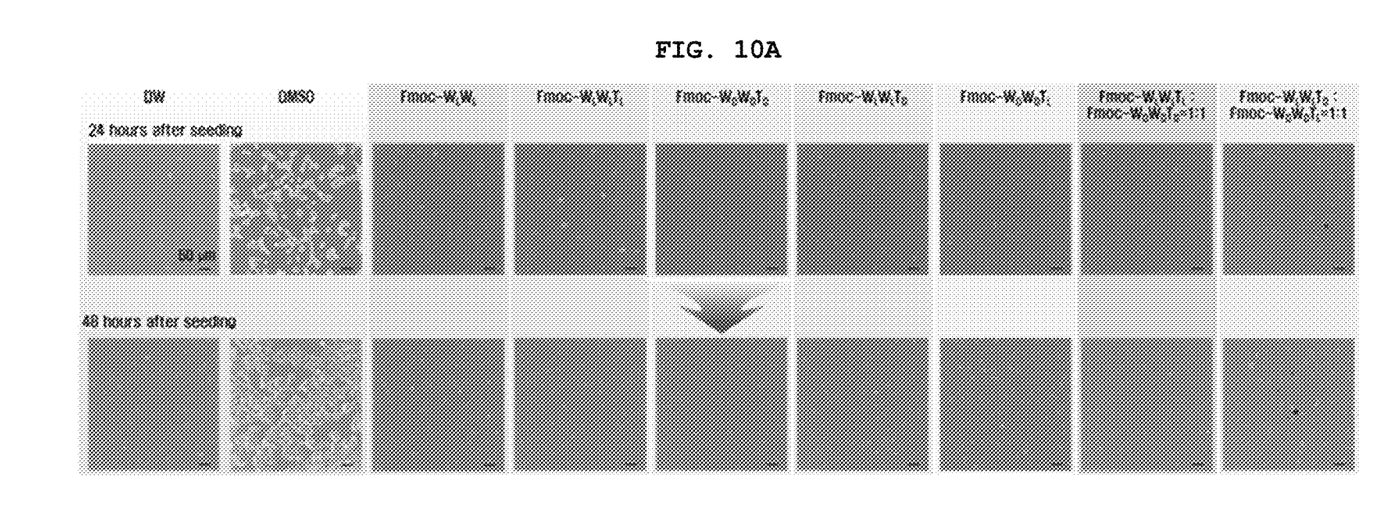
FIGS. 10A and 10B illustrates results confirming that the cryopreservation effect of Fmoc-$^L$W$^L$W$^L$T, Fmoc-$^D$W$^D$W$^D$T, a mixture of Fmoc-$^L$W$^L$W$^L$T and Fmoc-$^D$W$^D$W$^D$T, Fmoc-$^L$W$^L$W$^D$T, Fmoc-$^D$W$^D$W$^L$T, and a mixture of Fmoc-$^L$W$^L$W$^D$T and Fmoc-$^D$W$^D$W$^L$T on 293T cells is superior to that of Fmoc-$^L$W$^L$W$^L$T, Fmoc-$^D$W$^D$W$^D$T, and a mixture of Fmoc-$^L$W$^L$W$^L$T and Fmoc-$^D$W$^D$W$^D$T.
Figure 10B:
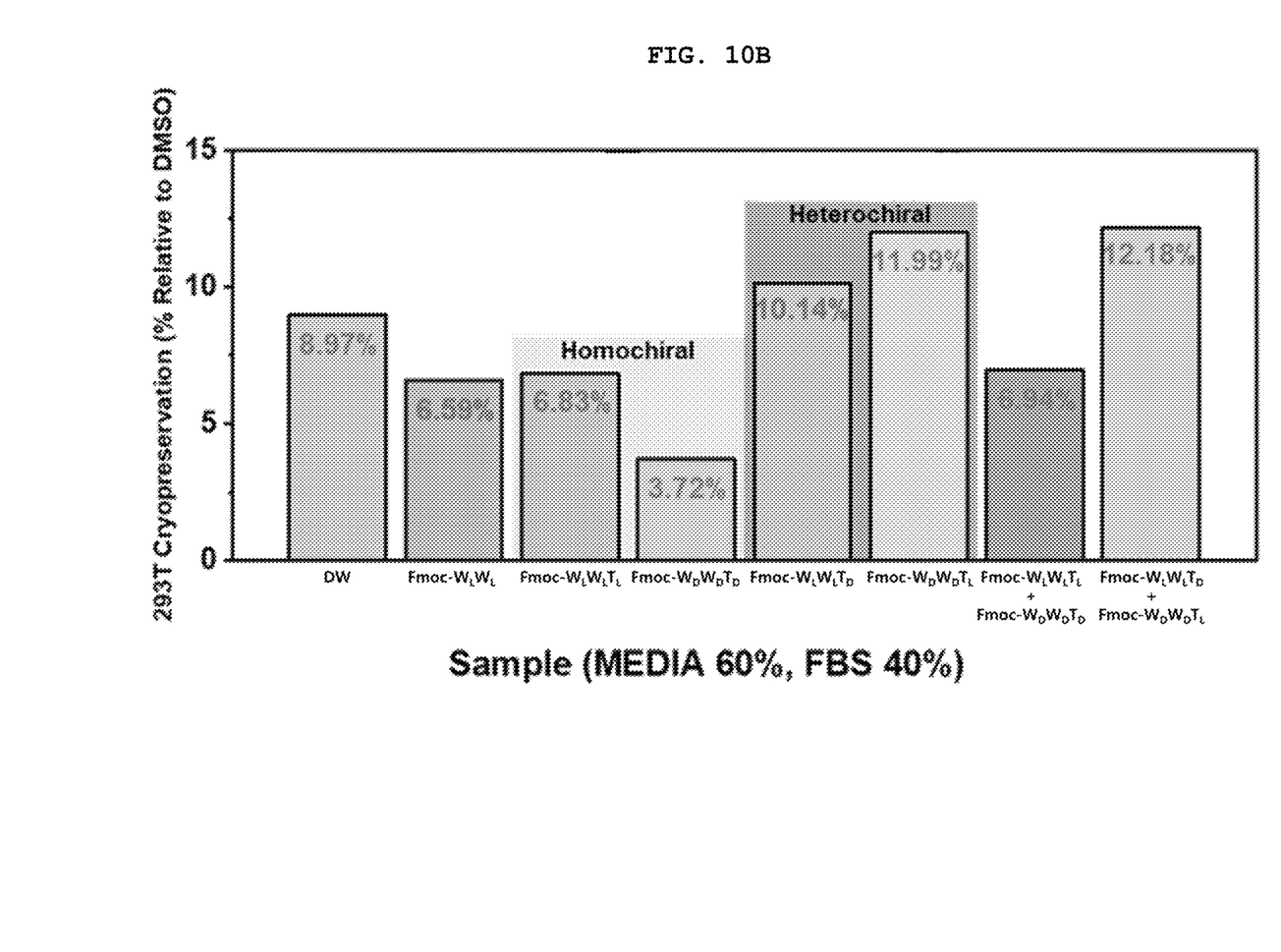

As can be seen from FIGS. 10A and 10B, when using Fmoc-$^LW^LW^DT$-$NH_2$ (LLD form) or Fmoc-$^DW^DW^LT$-$NH_2$ (DDL form) which is a heterochiral peptide, it exhibited higher cryopreservation efficacy than the case of using Fmoc-$^LW^LW^LT$-$NH_2$ (LLL form) or Fmoc-$^DW^DW^DT$-$NH_2$ (DDD form) which is a homochiral peptide. In addition, when using a racemic mixture in which heterochiral peptides, Fmoc-$^LW^LW^DT$-$NH_2$ (LLD form) and Fmoc-$^DW^DW^LT$-$NH_2$ (DDL form), were mixed, it exhibited higher cryopreservation efficacy than the case of using a racemic mixture in which homochiral peptides, Fmoc-$^LW^LW^LT$-$NH_2$ (LLL form) and Fmoc-$^DW^DW^DT$-$NH_2$ (DDD form), were mixed. This seems to be because the directions of the indole group of tryptophan (W) which is the functional group bound to the ice and the methyl group of threonine (T) are the same as each other, such that both functional groups inhibit access of water molecules.

What is claimed is:

1. An anti-freezing composition comprising at least one of a compound represented by Formula 1 and a compound represented by Formula 2:

[Formula 1]

wherein $R_1$ is —OH or —NH$_2$,

[Formula 2]

wherein $R_2$ is —OH or —NH$_2$.

2. The anti-freezing composition according to claim 1, wherein the anti-freezing composition comprises the compound represented by Formula 1 and the compound represented by Formula 2 in a molar ratio of 1:1.

3. A composition for cell or tissue cryopreservation comprising the composition of claim 1.

4. A composition for food cryopreservation comprising the composition of claim 1.

5. A composition for drug cryopreservation comprising the composition of claim 1.

6. An anti-freezing method comprising adding the composition of claim 1 to a sample subject to cryopreservation.

7. An anti-freezing method comprising adding the composition of claim 2 to a sample subject to cryopreservation.

8. The anti-freezing method according to claim 6, wherein the sample is at least one selected from the group consisting of a cell, a tissue, food and a drug.

* * * * *